United States Patent [19]

Papenfuhs

[11] Patent Number: 4,808,752
[45] Date of Patent: Feb. 28, 1989

[54] PROCESS FOR THE PREPARATION OF 2-AMINOPHENYL THIOETHERS

[75] Inventor: Theodor Papenfuhs, Frankfurt am Main, Fed. Rep. of Germany

[73] Assignee: Hoechst Aktiengesellschaft, Frankfurt am Main, Fed. Rep. of Germany

[21] Appl. No.: 892,598

[22] Filed: Jul. 31, 1986

[30] Foreign Application Priority Data

Aug. 5, 1985 [DE] Fed. Rep. of Germany ....... 3528033

[51] Int. Cl.$^4$ ..................... C07C 85/145; C07C 85/24
[52] U.S. Cl. .................................. 564/414; 564/413; 564/440; 560/17
[58] Field of Search ...................... 564/414, 440, 413; 560/17

[56] References Cited

U.S. PATENT DOCUMENTS 2,034,459  3/1935  Cole ................................. 564/413
3,102,142  8/1963  Horwitz et al. ................... 564/413
3,920,617  11/1975 Hirosawa et al. ................. 564/341
4,370,483  1/1983  Papenfuhs ......................... 548/165

FOREIGN PATENT DOCUMENTS 60-78959  5/1985  Japan ................................. 564/414

OTHER PUBLICATIONS

Smith, P. A. S., *The Chemistry of Open–Chain Organic Nitrogen Compounds*, vol. I (1965) p. 270.

*Primary Examiner*—Glennon H. Hollrah
*Assistant Examiner*—John A. Sopp

[57] ABSTRACT

A process for the preparation of 2-aminophenyl thioethers of the formula (1)

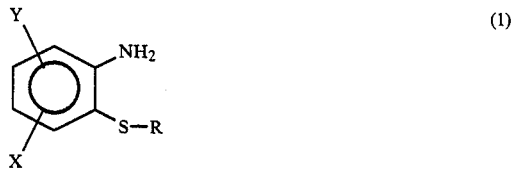

(1)

in which R represents an alkyl$\overline{C_1-C_6}$ group which can be substituted by hydroxyl, alkoxy$\overline{C_1-C_4}$, carboxyl, —COO-alkyl-$\overline{C_1-C_4}$, alkenyl$\overline{C_2-C_6}$ or phenyl groups or by the radical

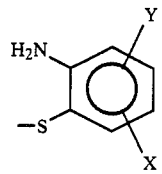

and X and Y are each a hydrogen or halogen atom or an alkyl$\overline{C_1-C_6}$, alkoxy$\overline{C_1-C_6}$ or nitro group, wherein the salts of the formula (4)

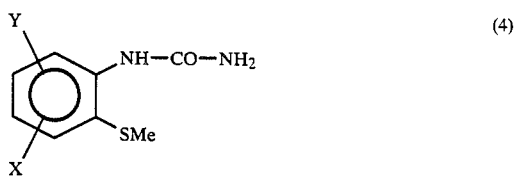

(4)

in which X and Y have the stated meanings and Me denotes an alkali metal atom or the equivalent amount of an alkaline earth metal atom, which are obtainable in a known manner by reacting 2-aminobenzothiazoles of the formula (3)

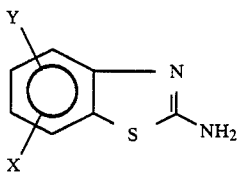

(3)

in which X and Y have the stated meanings, with an alkali metal or alkaline earth metal hydroxides in an alkali-stable anhydrous or virtually anhydrous solvent are reacted, in the isolated form or, advantageously in suspension in the mixture obtained in the ring-opening step, with an alkylating agent of the formula (2)

R—Z   (2)

in which R has the stated meaning and Z represents a halogen atom, or of the formula (2a)

(R'O)$_2$SO$_2$   (2a)

in which R' denotes an alkylC$_1$-C$_4$ group, or of the formula (2b)

Z—alkyleneC$_2$-C$_6$Z   (2b)

in which Z has the stated meaning, or with an alkylene-C$_2$-C$_3$ oxide at 0° to 100° C.

10 Claims, No Drawings

PROCESS FOR THE PREPARATION OF 2-AMINOPHENYL THIOETHERS

The present application relates to a process for the preparation of 2-aminophenyl thioethers, which are valuable intermediates for the preparation of dyes, crop protection agents and pharmaceuticals, the said process being improved in respect of industrial hygiene and waste water disposal and in terms of yield.

2-Aminophenyl thioethers of the general formula (1)

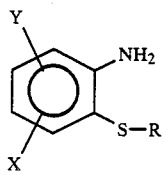
(1)

in which R represents an alkyl$_{C1-C6}$ group which can be substituted by hydroxyl, alkoxy$_{C1-C4}$, carboxyl, —COO-alkyl$_{C1-C4}$, alkenyl$_{C2-C6}$ or phenyl groups or the radical

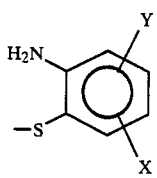

and X and Y each represents a hydrogen or halogen atom, for example a chlorine or bromine atom, or an alkyl$_{C1-C6}$, alkoxy$_{C1-C6}$ or nitro group, could be obtained to date industrially by alkylation of appropriate 2-nitrophenyl mercaptans with compounds of the general formula (2)

R—Z  (2)

in which R has the abovementioned meaning and Z represents a halogen atom, for example a chlorine or bromine atom, or with compounds of the general formula (2a)

(R'O)$_2$SO$_2$  (2a)

in which R' denotes an alkyl$_{C1-C4}$ group, or with compounds of the general formula (2b)

Z-alkylene$_{C2-C6}$Z  (2b)

in which Z has the abovementioned meaning, or with an alkylene$_{C2}$ or $_{C3}$ oxide followed by reduction of the nitro group, or by appropriate alkylation of the parent 2-aminophenyl mercaptans, which are obtained by reduction of the abovementioned nitro precursors, and in individual cases also by total alkaline hydrolysis of 2-aminobenzothiazoles or benzothiazthionium halides.

These synthesis variants thus proceed via free aryl mercaptans, giving rise to considerable problems with regard to industrial hygiene and waste water disposal. From the chemical point of view too, for the following reasons, there was also a need for a more effective process for the industrial preparation of the end compounds:

(a) The starting materials of the first synthesis variant, the 2-nitrophenyl mercaptans, are very sensitive to oxidation and inevitably result in reduced yields as the result of conversion to 2-nitrophenyl disulfides.

(b) The alkylation of the 2-aminophenyl mercaptans is, as a rule, not very selective, so that an expensive procedure to separate off N-alkylaminophenyl mercaptans or thioethers from the end product is indispensable, with the result that losses of yield likewise have to be accepted.

It has now been found, surprisingly, that the 2-aminophenyl thioethers of the abovementioned general formula (1) can be prepared by a method which completely avoids the stated disadvantages of the known processes, and in which the salts of the general formula (4)

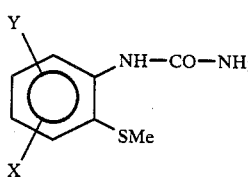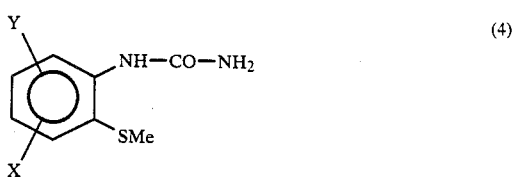
(4)

in which X and Y have the abovementioned meanings and Me denotes an alkali metal atom or the equivalent amount of an alkaline earth metal atom, preferably a sodium, potassium, half calcium or half magnesium atom, which are obtainable as intermediate compounds in high yields, in a known manner [European Pat. No. 0,039,483], by reacting 2-aminobenzothiazoles of the general formula (3)

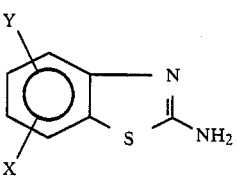
(3)

in which X and Y have the abovementioned meanings, with alkali metal or alkaline earth metal hydroxides in an alkali-stable anhydrous or virtually anhydrous solvent, such as ethanol, isobutanol, 1,2-dihydroxypropane or 1,3-dihydroxypropane, preferably ethylene glycol, glycerol, ethylene glycol monomethyl ether or ethylene glycol monoethyl ether, are reacted, in the isolated form or, advantageously, in suspension in the ring-opening mixture, with an alkylating agent of the general formula (2)

R—Z  (2)

in which R has the abovementioned meaning and Z represents a halogen atom, for example a chlorine or bromine atom, or of the general formula (2a)

(R'O)$_2$SO$_2$  (2a)

in which R' denotes an alkyl$_{C1-C4}$ group, or of the general formula (2b)

Z-alkylene$_{C2-C6}$Z  (2b)

in which Z has the abovementioned meaning, or with an alkylene$_{C2\ or\ C3}$ oxide, at temperatures of 0° C. to 100° C., preferably 20° C. to 70° C.

The 2-alkylmercaptophenylureas of the general formula (5)

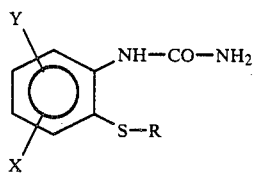

in which R, X and Y have the meanings mentioned further above, which have formed as intermediates in this process, are sufficiently stable to hydrolysis only in exceptional cases and can be isolated only when the procedure is carried out under absolutely anhydrous conditions. Under the reaction conditions, they are, as a rule, cleaved in a short time by the water present in the reaction mixture or subsequently added water to give the end products of the stated general formula (1), with formation of carbon dioxide and ammonia, according to the equation

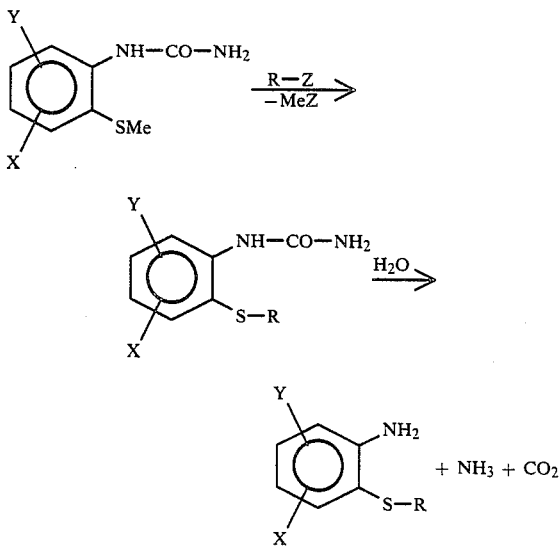

Thus, using the process according to the invention, it is possible to convert the industrially readily available 2-aminobenzothiazoles (German Pat. No. 2,801,991) to 2-aminophenyl thioethers in high yield and purity, in a one-pot reaction, by reaction with alkali metal or alkaline earth metal hydroxides followed by treatment with an alkylating agent of the stated formula (2), (2a) or (2b) or with an alkylene oxide. The process according to the invention avoids the use of free mercaptans and therefore does not give rise to any ecological problems or problems relating to industrial hygiene. Consequently, and because of the higher yield obtainable, the process according to the invention constitutes substantial technical progress.

Furthermore, it is surprising that, in the process according to the invention, no marked formation of by-products is observed. Although the lack of any N-alkylation can be explained by the protection of the amino group by the carbamoyl group, it was to be expected that, in the alkylation step (in the presence of water), acid liberated, even if only in traces and in a localized manner, would permit the acid-catalyzed cyclization of the 2-mercaptophenylurea to the corresponding 2-hydroxybenzothiazole according to European Pat. No. 0,039,483, this cyclization taking place very readily, or the hydrolysis of the urea group to give 2-aminothiophenol, this hydrolysis likewise being acid-catalyzed, and would therefore result in 2-aminophenyl thioethers which were contaminated with 2-hydroxybenzothiazole and/or 2-(alkyl)aminothiophenol (ethers).

The fact that these expected side reactions take place in no more than traces in the process according to the invention, so that a reaction which proceeds in virtually only one way to give the desired end products of the formula (1) results, was not foreseeable and appears extremely surprising in view of the fact that the reaction takes place in a complex manner in a plurality of synthesis steps.

The process according to the invention is carried out specifically as follows: an alkylating agent of the stated general formula (2), (2a) or (2b), for example a dialkyl sulfate, an alkylene dihalide or an alkyl halide, or an alkylene oxide, for example ethylene oxide or propylene oxide, is added in at least a molar amount, preferably in an excess of 5–25%, in the course of 0–5, preferably 0.5 to 2, hours, at temperatures of 0°–100° C., preferably 20°–70° C., to the 2-mercaptophenylurea salt of the stated general formula (4) in the form of the aqueous solution (or, if appropriate, suspension) resulting when the mixture from the ring-opening step is diluted with water, the said salt being obtainable, for example, according to European Pat. No. 0,039,483, Example 1, paragraph 1, and the 2-aminophenyl thioether formed is separated off from the reaction mixture by phase separation, filtration or extraction and subsequently freed from the adhering water or extracting agent.

It is of course also possible to start from isolated free 2-mercaptophenylurea, which can be prepared according to European Pat. No. 0,039,483, Example 1 (paragraph 1), and to suspend this compound in water and then neutralize it with a molar amount of an alkali metal or alkaline earth metal hydroxide or carbonate to give the salt of the stated general formula (4), and to use this in the process according to the inventionl. However, because of the problems described at the outset in connection with the use of free mercaptans, this variant is not a preferred one.

Particularly preferred, on the other hand, is the following variant, in which the reaction mixture consisting of the salt of the 2-mercaptophenylurea of the stated formula (4) and the solvent used for ring-opening (an alkanol, glycol, glycerol or glycol monoether), or a starting mixture prepared from an isolated 2-mercaptophenyl urea salt of the stated formula (4) [European Pat. No. 0,039,483, Examples 6–10] and one of the solvents used for ring-opening or another solvent which is inert to the alkylating agent (formula (2) or to the alkylene oxide under the reaction conditions (toluene, xylenes, chlorobenzene, chlorotoluenes, petroleum ether or chloroaliphatics), is reacted with the alkylating agent (formula (2)) or with the alkylene oxide at temperatures of 0° to 200° C., preferably 20° to 120° C., in at least a molar amount preferably an excess of 5 to 50%, in the Course of 1 to 10, preferably 2 to 6, hours, if appropriate under pressure. To work up the mixture, the end product (formula 1) is isolated by filtering, washing out the solvent and the resulting salt with water and drying or, particularly in the case of liquid or low-melting end products or those which are too readily soluble in the solvent, the mixture is concentrated by distillation, if appropriate after being filtered off from the salt formed, and the end product is then obtained in pure form by filtration, washing and drying or, particularly advantageously, by fractionation, preferably in a vacuum of 0.1 to 100 mm Hg.

The examples which follow are intended to illustrate the process according to the invention without restricting it. The parts stated are parts by weight.

EXAMPLE 1

82 parts of dimethyl sulfate are added, in the course of 15 minutes at 20° to 25° C., while stirring, to the solution of the sodium salt of 6-methyl-2-mercaptophenylurea, which solution is obtained according to Example 3 of European Pat. No. 0,039,483 by reacting 82 parts of 4-methyl-2-aminobenzothiazole with 50 parts of sodium hydroxide in glycerol and has been clarified with carbon. The reaction is then allowed to continue for 45 minutes.

The organic lower phase formed (density 1.15 g/ml) is separated off and fractionated over a short column. After a small first fraction (water), 72 parts of 3-methylmercapto-2-aminotoluene of the formula

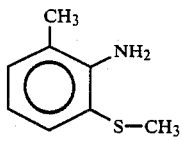

pass over at 132° C./20 mm Hg; this corresponds to a yield of 94.1% of theory, based on 4-methyl-2-aminobenzothiazole employed.

The product is virtually free of impurities and the gas chromatogram indicates a purity >99%, which is also confirmed by the diazotization value of 99.5%.

EXAMPLE 2

168 parts of the 2-mercaptophenylurea obtainable according to Example 1, paragraph 1, of European Pat. No. 0,039,483 are suspended in 500 parts of water, 60 parts of potassium hydroxide are added and the mixture obtained is transferred to a 1 liter autoclave. The autoclave is closed, 75 parts of methyl chloride are forced in and the autoclave is heated to 80° C. in the course of 1 hour, an internal pressure of about 2 bar being established; this pressure is reduced virtually completely to atmospheric pressure during stirring at 80° C. for a further hour. The autoclave is cooled and then emptied, and the organic lower phase formed (density 1.14 g/ml) is separated off and fractionated over a short column. 130 parts of 2-ethylmercaptoaniline of the formula

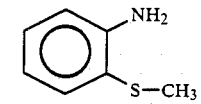

pass over as the main fraction, at 134° C./15 mm Hg; this corresponds to a yield of 93.5% of theory, based on 2-mercaptophenylurea employed.

The product has a diazotization value of 99.6% and is shown to be pure by the gas chromatogram.

EXAMPLES 3-8

If the procedure described in Example 2 is followed, but the methyl chloride is replaced with aliquot parts of the alkylating agents stated in Table 1 below, 2-aminophenyl alkyl ethers of the formula (6)

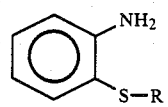

(6)

are obtained, likewise according to the invention, these compounds having the boiling points and yields listed in Table 1:

TABLE 1

| Example | Alkylating point | End product (R) | Boiling point | Yield % |
|---------|------------------|-----------------|---------------|---------|
| 3 | $(C_2H_5O)_2SO_2$ | $-C_2H_5$ | 144° C./15 mm Hg | 92.9% |
| 4 |  | $-CH_2CH_2-OH$ | 191° C./15 mm Hg | 89.8% |
| 5 | n-$C_3H_7Cl$ | $-(CH_2)_2-CH_3$ | 98° C./1 mm Hg | 93.8% |
| 6 | $CH_2=CH-CH_2Br$ | $-CH_2-CH=CH_2$ | 110° C./1 mm Hg | 89.5% |
| 7 |  | $-CH_2-CHOH-CH_3$ | 142° C./1 mm Hg | 87.0% |
| 8 | n-$C_4H_9Cl$ | $-(CH_2)_3-CH_3$ | 105° C./1 mm Hg | 94.8% |

EXAMPLE 9

112.25 parts of the sodium salt of 4-chloro-2-mercaptophenylurea, which salt is obtainable according to Example 6 of European Pat. No. 0,039,483, are suspended in 500 parts of water at room temperature. Thereafter, 100 parts of diethyl sulfate are added dropwise in the course of 30 minutes, while stirring, and the internal temperature should not exceed 25° C. during this procedure. The mixture is then heated to 80° C. in the course of 45 minutes and stirred for a further 30 minutes, and the organic lower phase formed is separated off and fractionated in vacuo. After an insignificant aqueous first fraction, 90.0 parts of 2-ethylmercapto-4-chloroaniline of the formula

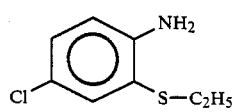

pass over at 167° C./20 mm Hg; this corresponds to a yield of 96.0% of theory, based on the sodium salt of 4-chloro-2-mercaptophenylurea employed.

The product is pure according to chromatography, and has a diazotization value of 99.7%.

EXAMPLES 10-15

If, in Example 9, the sodium salt of 4-chloro-2-mercaptophenylurea is replaced with aliquot parts of the salts of 2-mercaptophenylureas of the formula (7) which are listed in Table 2 below

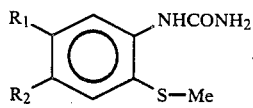 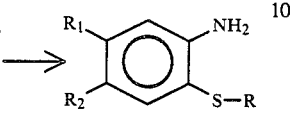

(7)     (8)

and the diethyl sulfate is replaced with aliquot parts of the alkylating agent likewise listed in Table 2, the 2-alkylmercaptoanilines of the formula (8) are obtained with the stated melting points or boiling points and in the yields shown in the table:

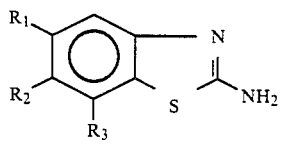

(9)

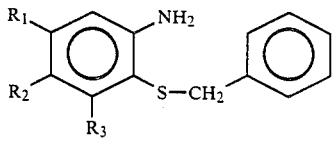

(10)

which are listed in Table 3 below, and the procedure is otherwise carried out in the manner stated, the 2-benzylmercaptoanilines of the formula (10) which are listed in Table 3 below are obtained with the melting points and yields stated there.

TABLE 2

| | Educt (7) | | | Product (8) | | | | |
|---|---|---|---|---|---|---|---|---|
| Example | Me | $R_1$ | $R_2$ | Alkylating agent | R | $R_1$ | $R_2$ | B.p.$_{(mm\ Hg)}$/m.p. | Yield |
| 10 | Na | H | H | Br—$CH_2$—$CH_2$—Br | Br—$CH_2$—$CH_2$—Br | H | H | M.p. 78° C. | 95.1% |
| 11 | K | $CH_3$ | H | $(CH_3O)_2SO_2$ | —$CH_3$ | $CH_3$ | H | B.p.$_{20}$: 130° C. | 91.5% |
| 12 | K | H | $OCH_3$ | $(CH_3O)_2SO_2$ | —$CH_3$ | H | $OCH_3$ | B.p.$_{20}$: 142° C. | 89.4% |
| 13 | Mg/2 | Cl | H | $(C_2H_5O)_2SO_2$ | —$C_2H_5$ | Cl | H | B.p.$_{20}$: 164° C. | 93.8% |
| 14 | Na | Br | H | $(C_2H_5O)_2SO_2$ | —$C_2H_5$ | Br | H | B.p.$_{20}$: 176° C. | 94.0% |
| 15 | Ca/2 | Cl | H | $CH_2$—$CH_2$ \\O/ | —$CH_2CH_2OH$ | Cl | H | B.p.$_5$: 186° C. | 87.8% |

EXAMPLE 16

A mixture of 150 parts of 2-aminobenzothiazole, 150 parts of solid sodium hydroxide and 300 parts of ethylene glycol is stirred for 6 hours at 130°-140° C. (Example 1 of European Pat. No. 0,039,483) and then cooled to 70° C., and 158 parts of benzyl chloride are added uniformly at this temperature in the course of 30 minutes. Stirring is continued for 2 hours at 70° to 80° C., the reaction mixture is allowed to run rapidly into 3000 parts of water, while stirring, and the mixture is cooled to 0° C. The 2-benzylmercaptoaniline of the formula

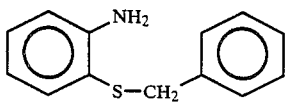

which separates out as granules during this procedure is filtered off with suction, washed with water and dried in vacuo at room temperature. 190 parts of a product of melting point 44° C. are obtained; this corresponds to a yield of 88.4% of theory, based on 2-aminobenzothiazole employed.

The product is pure according to gas chromatography and has a diazotization value of 99.3%.

EXAMPLES 17-21

If, in Example 16, the 2-aminobenzothiazole is replaced with aliquot parts of the 2-aminobenzothiazoles of the formula (9)

TABLE 3

| | Educt (9) | | | Product (10) | | | | |
|---|---|---|---|---|---|---|---|---|
| Example | $R_1$ | $R_2$ | $R_3$ | $R_1$ | $R_2$ | $R_3$ | Melting point | Yield |
| 17 | Cl | H | H | Cl | H | H | 54° C. | 92.8% |
| 18 | H | H | Cl | H | H | Cl | 41° C. | 89.2% |
| 19 | Cl | Cl | H | Cl | Cl | H | 72° C. | 94.0% |
| 20 | Br | H | H | Br | H | H | 56° C. | 92.1% |
| 21 | H | Cl | H | H | Cl | H | 61° C. | 90.3% |

EXAMPLE 22

168 parts of the 2-mercaptophenylurea obtainable according to Example 1, paragraph 1 of European Pat. No. 0,039,483 are dissolved in 500 parts by volume of 1N sodium hydroxide Solution at room temperature, 195 parts of β-bromopropionic acid are added all at once, and the mixture is stirred for 2 hours at room temperature. Thereafter, the mixture is heated to 100° C. in the course of 1 hour, stirred for a further 30 minutes at this temperature, cooled to 20° C. and brought to pH 3.0 with dilute hydrochloric acid, and the precipitated 2-aminophenyl-β-thiopropionic acid of the formula

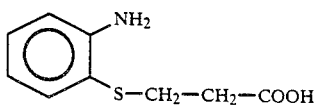

is filtered off, washed neutral with cold water and dried at 60° C. in vacuo. 162.5 parts of a product of melting point 86° to 87° C. are obtained; this corresponds to a yield of 82.5% of theory, based on 2-mercaptophenylurea employed. The product is pure according to chromatography and has a diazotization value of 99.8%.

EXAMPLE 23

A mixture f 150 parts of 2-aminobenzothiazole, 150 parts of solid sodium hydroxide and 300 parts of ethylene glycol is stirred for 6 hours at 130°–140° C. (Example 1 of European Pat. No. 0,039,483). The mixture is cooled to 45° C., 113 parts of chloroacetic acid are added so that the internal temperature does not exceed 50° C., and stirring is then continued for 2 hours at this temperature. The mixture is then heated to 80°–90° C. and kept at this temperature for 1 hour, and the resulting suspension of the sodium salt of 2-aminophenyl thioglycolic acid of the formula (11) is then allowed to run into a mixture of 2500 parts of water and 550 parts of 30% strength hydrochloric acid, the temperature increasing to 60° C. During this procedure, the 2-aminophenyl thioglycolic acid liberated undergoes rapid cyclization to give 3-oxo-dihydrobenzothiazine of the formula (12), which is the stable anhydride of the unstable free acid:

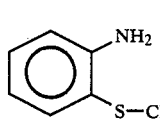 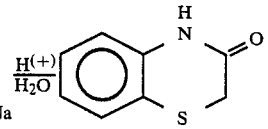

(11)　　　　　　　(12)

Stirring is continued for 30 minutes at 60° to 70° C., the mixture is cooled to room temperature and the precipitated product is filtered off, washed neutral with water and dried at 120° C. in a through-circulation oven. 150 parts of 3-oxo-dihydrobenzothiazine of melting point 175° C. are obtained; this corresponds to a yield of 90.0% of theory, based on 2-aminobenzothiazole employed.

The product is pure according to chromatography, and ring opening can be effected by heating the product with sodium hydroxide solution to produce a clear aqueous solution of sodium 2-aminophenyl thioglycolate, which has a purity of 99.4%, determined by indirect diazotization.

EXAMPLES 24–30

If, in Example 23, the 2-aminobenzothiazole is replaced with aliquot amounts of its derivatives of the formula (13) which are listed in Table 4 below, and this procedure is otherwise carried out in the manner stated, the 3-oxo-dihydrobenzothiazines (14) whose yield and melting point are stated in the table are obtained in comparable purity:

TABLE 4

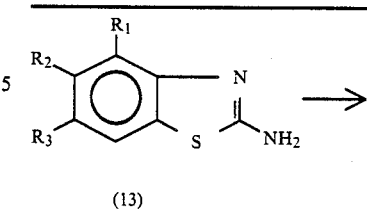

(13)

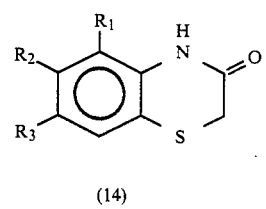

(14)

| | Educt (9) | | | Product (10) | | | | |
|---|---|---|---|---|---|---|---|---|
| Example | $R_1$ | $R_2$ | $R_3$ | $R_1$ | $R_2$ | $R_3$ | Melting Point | Yield |
| 24 | Cl | H | H | Cl | H | H | 153° C. | 92.5% |
| 25 | H | Cl | H | H | Cl | H | 205° C. | 94.5% |
| 26 | H | Cl | Cl | H | H | Cl | 204° C. | 91.9% |
| 27 | $CH_3$ | H | Cl | $CH_3$ | H | Cl | 190° C. | 93.2% |
| 28 | Cl | H | Cl | Cl | H | Cl | 164° C. | 95.6% |
| 29 | H | Br | H | H | Br | H | 206° C. | 94.6% |
| 30 | H | $NO_2$ | H | H | $NO_2$ | H | 242° C. | 91.8% |

I claim:

1. A process for the preparation of 2-aminophenyl thioethers of the formula (1)

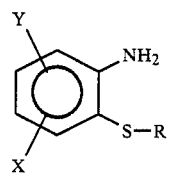

(1)

in which R represents an alkyl$\overline{C_1\text{-}C_6}$ group which can be substituted by hydroxyl, alkoxy$\overline{C_1\text{-}C_4}$, carboxyl, -COO-alkyl$\overline{C_1\text{-}C_4}$, alkenyl$\overline{C_2\text{-}C_6}$ or phenyl groups or by the radical

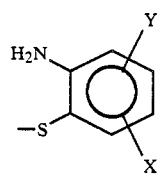

and X and Y are each a hydrogen or halogen atom or an alkyl$\overline{C_1\text{-}C_6}$, alkoxy$\overline{C_1\text{-}C_6}$ or nitro group, wherein the salts of the formula (4)

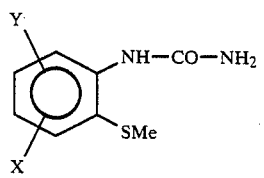

(4)

in which X and Y have the abovementioned meanings and Me denotes an alkali metal atom or the equivalent amount of an alkaline earth metal atom, which are obtainable in a known manner by reacting 2-aminobenzothiazoles of the formula (3)

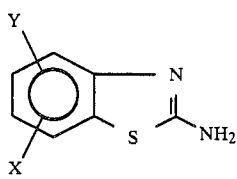

in which X and Y have the abovementioned meanings, with alkali metal or alkaline earth metal hydroxides in an alkali-stable, substantially anhydrous solvent, are reacted with an alkylating agent of the formula (2)

R—Z  (2)

in which R has the abovementioned meaning and Z represents a halogen atom, or of the formula (2a)

 (2a)

in which R' denotes an alkyl $C_1$-$C_4$ group, or of the formula (2b)

 (2b)

in which Z has the abovementioned meaning, or with an alkylene $C_2$ or $C_3$-oxide at temperatures of 0° to 100° C. in the presence or absence of water, with the proviso that if the reaction with said alkylating agent is carried out in the absence of water, water is added immediately after said reaction.

2. A process according to claim 1, wherein said salts are reacted in the isolated form.

3. A process according to claim 1, wherein said salts are reacted in suspension in the mixture obtained in the ring opening step.

4. A process for the preparation of a 2-aminophenyl thioether of the formula (1)

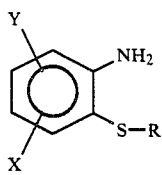 (1)

in which R represents a $C_1$-$C_6$ alkyl group which is unsubstituted or substituted by hydroxy, $C_1$-$C_4$ alkoxy, carboxyl, —COO—($C_1$ to $C_4$-alkyl), $C_2$-$C_6$-alkenyl, or a phenyl group, or by the radical

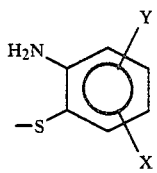

and X and Y are each a hydrogen or halogen atom or a $C_1$-$C_6$ alkyl, $C_1$-$C_6$ alkoxy or nitro group, said process comprising: reacting a salt of the formula (4)

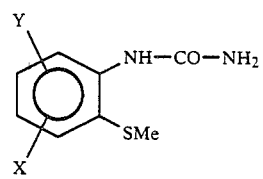 (4)

in which X and Y are as previously defined and Me denotes an alkali metal atom or the equivalent amount of an alkaline earth metal atom, with an alkylating agent of the formula (2)

R—Z  (2)

in which R is as defined previously and Z represents a halogen atom, or of the formula (2a)

$(R'O)_2SO_2$  (2a)

in which R' denotes a $C_1$-$C_4$-alkyl group, or of the formula (2b)

Z—($C_2$ to $C_6$-alkylene)—Z  (2b)

in which Z is as defined previously, or with our alkylene $C_2$- or $C_3$-oxide, at a temperature in the range of 0° to 100° C., with hydrolysis of the —NH—CO—NH$_2$ group to —NH$_2$, the water for said hydrolysis either being present during the reaction with the alkylating agent and hence available for said hydrolysis, or being added after said reaction.

5. A process according to claim 4, comprising the steps of:
obtaining the salt of formula (4) from a 2-aminobenzothiazole of the formula (3)

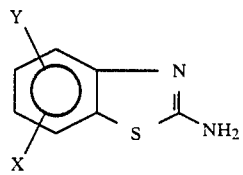 (3)

wherein X and Y are as defined previously, by reacting the compound of formula (3) with an alkali metal or alkaline earth metal hydroxide in an alkali-stable, substantially anhydrous solvent, thereby obtaining a suspension of the salt of formula (4) in said solvent.

6. A process according to claim 5, wherein said suspension of the salt of formula (4) is reacted with the alkylating agent.

7. A process according to claim 5, wherein said salt of formula (4) is first isolated and then reacted with the alkylating agent.

8. A process according to claim 5 wherein said suspension is reacted with the alkylating agent in the absence of water, and water is added subsequent to the reaction with the alkylating agent to effect said hydrolysis.

9. A process according to claim 5, in which R represents a $C_1$-$C_6$ alkyl group which is unsubstituted or substituted by hydroxyl, $C_2$ to $C_6$-alkenyl, carboxyl, or phenyl.

10. A process according to claim 5, wherein any acid present during said hydrolysis is substantially limited to acid liberated in traces and in a localized manner during the reaction with the alkylating agent.

* * * * *